United States Patent [19]
Ashley et al.

[11] Patent Number: 5,855,910
[45] Date of Patent: Jan. 5, 1999

[54] CATIONIC PHOSPHOLIPIDS FOR TRANSFECTION

[75] Inventors: Gary W. Ashley, Alameda, Calif.; Robert C. MacDonald, Evanston; Miho Shida, Barrington, both of Ill.

[73] Assignee: Northwestern University, Evanston, Ill.

[21] Appl. No.: 470,928

[22] Filed: Jun. 6, 1995

Related U.S. Application Data

[62] Division of Ser. No. 220,376, Mar. 29, 1994, Pat. No. 5,651,981.

[51] Int. Cl.[6] .................................................. A61K 9/127
[52] U.S. Cl. .............................. 424/450; 935/54
[58] Field of Search ........................... 424/450; 558/106, 558/113; 935/54

[56] References Cited

U.S. PATENT DOCUMENTS

| | | |
|---|---|---|
| 4,480,041 | 10/1984 | Myles et al. . |
| 4,493,832 | 1/1985 | Teraji et al. . |
| 4,562,179 | 12/1985 | Teraji et al. . |
| 4,897,355 | 1/1990 | Eppstein et al. . |
| 4,946,787 | 8/1990 | Eppstein et al. . |
| 4,948,576 | 8/1990 | Verdicchio et al. . |
| 5,153,347 | 10/1992 | Lloyd . |
| 5,344,930 | 9/1994 | Riess et al. . |
| 5,420,330 | 5/1995 | Brush . |

FOREIGN PATENT DOCUMENTS

| | | |
|---|---|---|
| 0092190 | 10/1983 | European Pat. Off. . |
| 0099068 | 1/1984 | European Pat. Off. . |
| 0394111 | 10/1990 | European Pat. Off. . |
| WO9116024 | 10/1991 | WIPO . |
| WO9319768 | 10/1993 | WIPO . |
| WO9405624 | 3/1994 | WIPO . |

OTHER PUBLICATIONS

Kan Biochemistry #30, p. 7759, 1991.
Schroeder Biochemistry #28, p. 5992 1989.
Barenholz Biochemistry #15, p. 2441, 1976.
Koiv Chemistry & Physics of Lipids 72 p. 77 (1994.
Bruzik et al., *J. Org. Chem.* 51:2368–2370 (1986).
Chen, J–S et al., *Chemical Abstracts*, vol. 73, No. 24844.
Qiu, X. et al., *J. Org. Chem.* 59:537–543 (1994).
Law, S–J. et al., *Tetrahedron Letters* 27:271–274 (1986).
Graham and Van der Eb, *Virology* 52, 456 (1973).
Kawai and Nishizawa, *Mol. Cell Biol.* 4, 1172 (1984).
Neumann et al., *EMBO Journal* 1, 841 (1982).
Graessmann and Graessman in *Microinjection and Organelle Transplantation Techniques*, pp. 3–13 (Cells et al., Eds., Academic Press 1986).
Cudd and Nicolau, in *Liposome Technology*, pp. 207–221 (G. Gregoriadis, Ed., CRC Press 1984).
Cepko et al., *Cell* 37, 1053 (1984).
Schaffner, *Proc. Natl. Acad. Sci. USA* 77, 2163 (1980).
Magee et al., *Biochim. Biophys. Acta* 451, 610–618 (1976).
Straub et al., *Infect. Immun.* 10, 783–792 (1974).
Martin and MacDonald, *J. Cell Biol.* 70, 515–526 (1976).
Magee et al., *J. Cell. Biol.* 63, 492 (1974).
Steger and Desnick, *Biochim. Biophys. Acta*, 464, 530 (1977).
Juliano and Stamp, *Biochem. Pharma.* 27, 2–27 (1978).
Mayhew et al., *Cancer Res.* 36, 4406 (1976).
Kimelberg, *Biochim. Biophys. Acta* 448, 531 (1976).

(List continued on next page.)

*Primary Examiner*—Gollamudi S. Kishore
*Attorney, Agent, or Firm*—Banner & Witcoff LTD

[57] ABSTRACT

A novel class of cationic phospholipids and novel method for their synthesis are disclosed. The class of phospholipids comprises phosphotriester derivatives of phosphoglycerides and sphingolipids. It has been unexpectedly found that liposomes comprising one or more of these cationic phospholipids are effective in the lipofection of nucleic acids. These novel phospholipids are particularly attractive because of they are not only effective in lipofection, but are extremely cheap and easy to make.

3 Claims, 2 Drawing Sheets

OTHER PUBLICATIONS

Thierry et al. in *Gene Regulation: Biology of Antisense RNA and DNA*, p. 147 (Erickson and Izant, Eds., Raven Press, New York, 1992).
Hug and Sleight, *Biochim. Biophys. Acta* 1097, 1 (1991).
Nicolau and Cudd, *Crit. Rev. Ther. Drug Carr. Sys.* 6, 239 (1989).
Senior et al., *Biochim. Biophys. Acta* 1070, 173 (1991).
Felgner et al., *Proc. Natl. Acad. Sci. USA* 84, 7413 (1987).
Rose et al., *BioTechniques* 10, 520 (1991).
Malone et al., *Proc. Natl. Acad. Sci. USA* 86, 6077 (1989).
Zhou and Haung, *J. Controlled Release* 19, 269 (1992).
Hawley–Nelson et al., *Focus* 15, 73 (1990, BRL publications).
Farhood et al., *Biochim. Biophys. Acta* 1111, 239 (1992).
Gao and Huang, *Biochim. Biophys. Res. Comm.* 179, 280 (1991).
Holt et al., *Neuron* 4, 203 (1990).
Malone, *Focus* 11, 4 (1989, BRL publications).
Ono et al., *Neurosci. Lett.* 117, 259 (1990).
Brigham et al., *Am. J. of Med. Sci.* 298, 278 (1989).
Nabel et al., *Science* 249, 1285 (1990).
Lim et al., *Circulation* 83, 2007 (1991).
Hazinski, *Sem. Perinatol.* 16, 200 (1992).
Yosimura et al., *Nucleic Acids Res.* 20, 3233 (1992).
Hyde et al., *Nature* 362, 250 (1993).
Ballas et al., *Biochim. et Biophys. Acta* 939, 8 (1988).
Pinnaduwage et al., *Biochim. et Biophys. Acta* 985, 33 (1989).
Taylor et al., *Nucleic Acids Res.* 20, 4559–4565 (1992).
Leventis and Sivius, *Biochim. et Biophys. Acta* 1023, 124 (1990).
Düzgünes and Felgner, *Methods in Enzymology* 221, 303 (1993).
Smith et al., *Biochim. Biophys. Acta* 1154, 327 (1993).
Maccarrone et al., *Biochem. Biophys. Res. Comm.* 186, 1417 (1992).
Gershon et al., *Biochem.* 32, 7143–7151 (1993).
Legendre and Szoka, *Pharm. Res.* 9, 1235 (1992).
Renkonen, *Biochim. et Biophys. Acta* 152, 114 (1968).
Gorman et al., *Mol. Cell. Biol.* 2, 1044 (1982).
de Wet et al., *Mol. Cell. Biol.* 7, 725 (1987).
Jarnagin et al., *Nucl. Acids Res.* 20, 4205 (1992).
Zhu et al., *Science* 261, 209–211 (1993).
Stribling et al., *Proc. Natl. Acad. Sci. USA* 89, 11277–11281 (1992).
*Chemical Abstracts* 73:310, Abstract No. 024844 (1970).
Chen, J.–S. and Barton, P.G., *Can. J. Biochem.* 48:585–593 (1970).
Liposome Technology, vol. 1, Chapter 1, pp. 1–37 (G. Gregoriadis, Ed., CRC Press, 1993).
Liposome Technology, vol. 1, Chapter 3, pp. 49–65 (G. Gregoriadis, Ed., CRC Press, 1993).
Liposome Technology, vol. 1, Chapter 27, p. 487–499 (G. Gregoriadis, Ed., CRC Press, 1993).
Liposome Technology, vol. 1, Chapter 28, pp. 501–525 (G. Gregoriadis, Ed., CRC Press, 1993).
Booklet from Nov. 1, 1991 Northwestern University Chemistry Department Fall Symposium, entitled "Advances in Nucleic Acids Chemistry".
List of Poster presented at Nov. 1, 1991 Northwestern University Chemistry Department Fall Symposium, entitlted "Advances in Nucleic Acids Chemistry".
Abstract of Poster by Gary W. Ashley, Miho Shida and Robert MacDonald, presented at Nov. 1, 1991 Northwestern University Chemistry Department Fall Symposium.

Nothing  Dye  0%  50%  100%

CATIONIC PHOSPHOLIPIDS FOR TRANSFECTION

This is a divisional of application Ser. No. 08/220,376 filed Mar. 29, 1994 now U.S. Pat. No. 5,651,981.

BACKGROUND OF THE INVENTION

1. Field of the Invention

This invention relates to novel cationic phospholipids and methods for making them. This invention also relates to novel liposomes and aggregates comprising the phospholipids of the present invention that are useful for the delivery of nucleic acids and drugs to cells, both in vitro and in vivo. This invention also relates to the treatment of diseases by gene therapeutics involving transfection with DNA and introduction into cells of antisense nucleotides, as well as stable transfection with DNA engineered to become incorporated into the genome of living cells.

2. Description of the Related Art

The introduction of foreign nucleic acids and other molecules is a valuable method for manipulating cells and has great potential both in molecular biology and in clinical medicine. Many methods have been used for insertion of endogenous nucleic acids into eukaryotic cells. E.g., Graham and Van der Eb, *Virology* 52, 456 (1973) (co-precipitation of DNA with calcium phosphate); Kawai and Nishizawa, *Mol. Cell. Biol.* 4, 1172 (1984) (polycation and DMSO); Neumann et al., *EMBO Journal* 1, 841 (1982) (electroporation); Graessmann and Graessmann in *Microinjection and Organelle Transplantation Techniques,* pp. 3–13 (Cells et al., Eds., Academic Press 1986) (microinjection); Cudd and Nicolau in *Liposome Technology,* pp. 207–221 (G. Gregoriadis, Ed., CRC Press 1984) (liposomes); Cepko et al., *Cell* 37, 1053 (1984) (retroviruses); and Schaffner, *Proc. Natl. Acad. Sci. USA* 77, 2163 (1980) (protoplast fusion). Both transient and stable transfection of genes has been demonstrated.

Some of the first work on liposome delivery of endogenous materials to cells occurred some twenty years ago. Foreign nucleic acids were introduced into cells (Magee et al., *Biochim. Biophys. Acta* 451, 610–618 (1976), Straub et al., *Infect. Immun.* 10, 783–792 (1974)), as were foreign lipids (Martin and MacDonald, *J. Cell Biol.* 70, 515–526 (1976)), Proteins (Magee et al., *J. Cell. Biol.* 63, 492 (1974), Steger and Desnick, *Biochim. Biophys. Acta* 464, 530 (1977) ), fluorescent dyes (Leventis and Silvius), and drugs (Juliano and Stamp, *Biochim. Pharm.* 27, 21–27 (1978), Mayhew et al., *Cancer Res.* 36, 4406 (1976), Kimelberg, *Biochim. Biophys. Acta* 448, 531 (1976)), all using positively charged lipids.

Of the many methods used to facilitate entry of DNA into eukaryotic cells, cationic liposomes are among the most efficacious and have found extensive use as DNA carriers in transfection experiments. See, generally, Thierry et al. in *Gene Regulation: Biology of Antisense RNA and DNA,* p. 147 (Erickson and Izant, Eds., Raven Press, New York, 1992); Hug and Sleight, *Biochim. Biophys. Acta* 1097, 1 (1991); and Nicolau and Cudd, *Crit. Rev. Ther. Drug Carr. Sys.* 6, 239 (1989) The process of transfection using liposomes is called lipofection. Senior et al., *Biochim. Biophys. Acta* 1070, 173 (1991), suggested that incorporation of cationic lipids in liposomes is advantageous because it increases the amount of negatively charged molecules that can be associated with the liposome. In their study of the interaction between positively charged liposomes and blood, they concluded that harmful side-effects associated with macroscopic liposome-plasma aggregation can be avoided in humans by limiting the dosage.

Feigner et al., *Proc. Natl. Acad. Sci. USA* 84, 7413 (1987), demonstrated that liposomes of dioleoylphosphatidylethanolamine (DOPE) and the synthetic cationic lipid N-[1-(2, 3-dioleyloxy)propyl]-N,N,N-trimethylammonium chloride (DOTMA) are capable of both transiently and stably transfecting DNA. Rose et al., *BioTechiques* 10, 520 (1991), tested lipofection with liposomes consisting of DOPE and one of the cationic lipids cetyldimethylethylammonium bromide (CDAB), cetyltrimethylethylammonium bromide (CTAB), dimethyldioctadecylammonium bromide (DDAB), methylbenzethonium chloride (MBC) and stearylamine. All of the liposomes (except that with CTAB) successfully transfected DNA into HeLa cells. At high concentrations, however, CDAB and MBC caused cell lysis. Only DDAB was found to be effective in mediating efficient DNA transfection into a variety of other cell lines. Malone et al., *Proc. Natl. Acad. Sci. USA* 86, 6077 (1989), successfully transfected RNA, in vitro, into a wide variety of cells lines. Zhou and Haung, *J. Controlled Release* 19, 269 (1992), disclosed successful lipofection by DOPE liposomes stabilized in the lamellar phase by cationic quaternary ammonium detergents. The authors noted, however, that the relatively high cytotoxicity of these compounds would limit their use in vivo.

Hawley-Nelson et al., *Focus* 15, 73 (1990, BRL publications), disclosed the cationic lipid "LIPOFECTAMINE", a reagent containing 2,3-dioleyloxy-N-[2(sperminecarboxyamido)ethyl]-N,N-dimethyl-1-propanaminium trifluoroacetate (DOSPA). "LIPOFECTAMINE" was found to have higher transfection activity than several monocationic lipid compounds ("LIPOFECTIN", "LIPOFECTACE", and DOTAP) in six of eight cell types tested. They observed toxicity when both lipid and DNA were included in the same mixture.

Both Farhood et al., *Biochim. Biophys. Acta* 1111, 239 (1992), and Gao and Huang, *Biochem. Biophys. Res. Comm.* 179, 280 (1991), disclose cationic derivatives of cholesterol as components of liposomes capable of transfecting cells in vitro.

Liposomes comprising cationic lipids may also find use as carriers for gene therapy in in vivo applications. Some of the first in vivo applications of delivery of endogenous materials via liposomes was demonstrated twenty years ago. See, e.g., Straub et al., supra, and Magee et al., supra, (nucleic acids), and Mayhew et al., supra (drugs), Holt et al., *Neuron* 4, 203 (1990), describe a DOTMA dioleoxylphosphatidylethanolamine liposome that successfully transfected a vector expressing luciferase cDNA into embryonic brain of Xenopus in vivo.

Malone, *Focus* 11, 4 (1989, BRL publications), reported a similar study on Xenopus neural tissue as did Ono et al., *Neurosci. Lett.* 117, 259 (1990), in mouse brain.

Brigham et al., *Am J. Med. Sci.* 298, 278 (1989), disclosed intravenous injection of "LIPOFECTIN" and chloramphenicol acetyl transferase (CAT) plasmid into mouse lungs.

Nabel et al., *Science* 249, 1285 (1990), reported the expression of a β-galactosidase gene in a specific arterial segment in vivo in Yucatan pigs by DNA transfection with cationic liposomes. Lim et al., *Circulation* 83, 2007 (1991), disclosed in vivo gene transfer of reporter genes (β-galactosidase and luciferase) into arteries of dogs using cationic liposomes.

Hazinski, *Sem. Perinatol.* 16, 200 (1992) disclosed cationic liposome-mediated transfer of fusion reporter genes to the epithelial cells and transient protein expression via direct injection of DNA-liposome solution into the trachea.

Yosimura et al., *Nucleic Acids Res.* 20, 3233 (1992) demonstrated successful in vivo lipofection of the cystic fibrosis trans-membrane conductance regulator gene (CFTR) into airway epithelium of mice using the cationic liposome "LUPOFECTIN". Hyde et al., *Nature* 362, 250 (1993), also disclosed lipofection of CFTR using "LIPO-FECTIN". They demonstrated successful delivery of the gene to epithelia of the airway and to alveoli deep in the lung of transgenic mice.

Several cationic amphiphiles have been reported as transfection agents. Ballas et al., *Biochim. et Biophys. Acta* 939, 8 (1988), reported the successful lipofection of tobacco mosaic virus RNA into tobacco and petunia protoplasts via liposomes composed of phosphatidylcholine (PC), cholesterol, and the hydroxyl form of the quaternary ammonium detergent diisobutylcresoxyethoxyethyldimethylbenzylammonium (DEBDA [OH$^-$]). Liposomes lacking the quaternary ammonium detergent practically failed to transfect the RNA. Importantly, Ballas et al. also observed that RNA and DNA complexed to liposomes bearing DEBDA[OH$^-$] were highly resistant to added RNAses and DNAses.

Pinnaduwage et al., *Biochim. et Biophys. Acta* 985, 33 (1989), disclosed the lipofection of pSV2 CAT plasmid DNA into mouse L929 fibroblasts using sonicated liposomes comprising DOPE and a quaternary ammonium detergent (dodecyl-, tetradecyl-, or cetyl-trimethylammonium bromide). Pinnaduwage et al. note, however, that a major drawback of using single chain amphiphiles such as detergents for drug delivery is their toxicity.

Taylor et al., *Nucleic Acids Res.* 20, 4559–4565 (1992) successfully transfected both RNA ribozymes and chimeric RNA-DNA ribozymes with "LIPOFECTIN".

Leventis and Sivius, *Biochim. et Biophys. Acta* 1023, 124 (1990), disclosed several cationic amphiphiles based on a hydrophobic cholesteryl or dioleoylglyceryl moiety whose hydrophobic and cationic portions are linked by ester bonds, which should facilitate degradation in animal cells. Leventis and Sivius demonstrated successful lipofection of plasmid pSV2 CAT into CV-1 and 3T3 cells using liposomes containing the cationic amphiphiles 1,2-dioleoyl-3-(4'-trimethylammonio)butanoyl-sn-glycerol (DOTB), DOTAP and cholesteryl (4'-trimethylammonio)butanoate (ChoTB).

Düzgünes and Felgner, *Methods in Enzymology* 221, 303 (1993), describe methods for transfection of nucleic acids. They teach that when preparing complexes of DNA and "LIPOFECTIN" for transfection, a net positive charge is desired, and the corresponding ratio of the weight of lipid to nucleic acid is about 4–10. They warn, however, that optimization should be undertaken for each cell line to be transformed.

The precise way in which nucleic acids and phospholipids (and other amphiphiles) interact and the structure formed before and during the transfection process is not well understood. Commonly, the nucleic acids are said to be entrapped within a lipid bilayer, which is the classic definition of "liposome." There is also a belief, however, that the nucleic acid does not become entrapped, but forms some other sort of aggregate with the phospholipids. See, e.g., Smith et al., *Biochim. Biophys. Acta* 1154, 327 (1993), for several models of lipid/nucleic acid interaction. Maccarrone et al., *Biochem. Biophys. Res. Comm.* 186, 1417 (1992), disclosed that liposome-DNA aggregate size and shape was a function of the ratio of the amount DNA to that of phospholipid. They concluded that DNA binds to the outer surface of liposomes, which then cluster into irregular spherical aggregates. They also noted that plasmid length had no effect on binding to liposomes. Gershon et al., *Biochem.* 32, 7143–7151 (1993) examined the fluorescence of ethidium bromide in the presence of DOTMA and DNA. They observed an -abrupt drop in its fluorescence when DNA/ethidium bromide is titrated with DOTMA to the point of near electrical neutrality. Electron microscopy of the complex revealed an abrupt condensation of the DNA at the point of neutrality. It is evident from these experiments that, at least for DOTMA, but probably for most cationic lipids as well, that the structure of the complex changes at charge neutrality, and concomitantly the DNA becomes very compactly organized into a structure that is evidently quite different from a vesicular liposome. Legendre and Szoka, *Pharm. Res.* 9, 1235 (1992), studied in vitro lipofection using a DOTMA:DOPE liposome and concluded that the liposome probably uses at least two pathways to introduce DNA into cells: fusion with the plasma membrane and endocytosis.

It should be recognized that virtually all of the compounds described thus far in the literature as "cationic lipids" are, in fact, cationic amphiphiles or cationic detergents. The term "lipid" refers to a natural product. Most lipids contain fatty acids as their major hydrophobic component, although some (such as cholesterol, sphingolipids and polyisoprenoids) have other hydrophobic structures.

Reagent mixtures of phosphatidylethanolamine (PE) with either DOTMA or dioctadecyldimethylammonium bromide (DDMB) are commercially available (e.g., from Promega). DOTMA-based transfection reagents are expensive due to the synthetic complexity of the cationic lipid, while the simple detergents are cheap but require dilution of the cationic species with relatively expensive PE. Both show significant cytotoxicity (especially single-chain compounds). The underlying causes of the cytotoxicity are unclear, but the difficulty or impossibility of metabolizing these materials can only exacerbate this problem during long-term use. Cytotoxicity is not a pressing problem for transient transfection procedures, but it must be solved prior to the use of liposome transfection in therapeutic applications. Consequently, cheaper, safer, and more effective lipids useful in lipofection technology are desirable.

As is further described below, the present invention provides novel compounds having these attributes. This new class of compounds comprise phosphoglyceride derivatives having a modified phosphodiester linkage, wherein a non-bridging oxygen is alkylated, producing a phosphate triester. In so alkylating the phosphate moiety, the negative charge on the oxygen is eliminated.

Methylation of phosphodiester linkages to produce P(O)-methyl derivatives has been reported. Renkonen, *Biochim. et Biophys. Acta* 152, 114 (1968). Although treatment of phosphatidylcholine (PC) with diazomethane yields dimethyl phosphatidic acid with loss of the choline residue, O-methyl phosphatidylcholinium has been isolated in low yield from this reaction in the presence of triethylammonium hydrochloride as proton donor. Diazomethane on a preparative scale is extremely hazardous, however, and the number of readily available diazoalkanes is limited. We also note that methyl phosphatidylcholinium is relatively unstable. Thus, a more efficient method for producing phosphate triester derivatives of phosphatidylcholine is desirable.

SUMMARY OF THE INVENTION

We disclose here a novel class of cationic phospholipids that are capable of generating liposomes. The phospholipids of the present invention are derived from parent phosphoglyceride compounds having the structures:

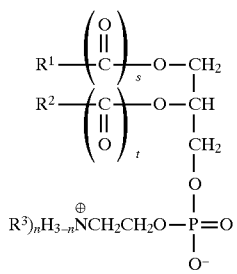

wherein one or both of $R^1$ and $R^2$ typically are hydrocarbon chains having from 1 to about 24 carbons, optionally substituted with a dansyl, NBD (nitrobenzofurazan), DPH (1,6-diphenyl-1,3,5-hexatriene), carbocyclic group or a heterocyclic moiety, s and t are independently 0 or 1, $R^3$ is hydrogen or methyl, and n is 0, 1, 2, or 3. In a preferred embodiment of the present invention, the parent phosphoglyceride compound is naturally occurring. In a particularly preferred embodiment, the compound is phosphatidylcholine.

The novel phospholipids of the present invention obtained by alkylating the above reactant compounds have the following structure:

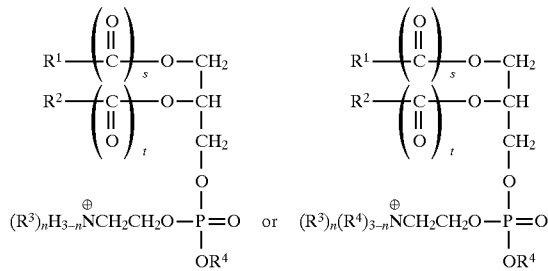

wherein all definitions described above for the parent compound hold, $R^4$ is an optionally substituted $C_1$ to about $C_{24}$ hydrocarbon chain.

These lipids are attractive for a number of reasons. First, we have found that liposomes and aggregates comprising these cationic phospholipids are effective in the transfection of nucleic acids, having efficacy comparable to that of the commonly used commercial product "LIPOFECTIN". Second, most of the phospholipids of the present invention are easily made from cheap and readily available starting materials in a one step synthesis. And finally, most of the phospholipids of the present invention are derived from a naturally occurring parent compound, thereby providing a means for cellular metabolism and minimizing the cytotoxicity of these compounds under chronic administration.

We also disclose compounds generated from sphingophospholipids, phospholipids having a phosphorylcholine polar group, identical to that of phosphatidylcholine, but with ceramide in place of dialkylglycerol in the hydrophobic portion of the molecule. Sphingophospholipids are alkylated in the same way as the phosphoglycerides discussed above, generating the corresponding cholinium compounds. The general structure of the sphingophospholipids is:

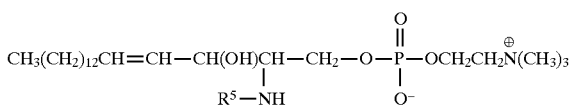

where $R_5$ is a fatty acid or related carboxylic acid of the same type as $R^1$, supra. Alkylation is at the same position (on the phosphate oxygen) as in the phosphoglycerides.

We also present a novel method of synthesizing the cationic phospholipids of the present invention. The preferred method comprises alkylating a parent phospholipid compound (having a structure defined above) by contacting it with a $R^4$-trifluoromethanesulfonate (triflate) in a suitable solvent, wherein $R^4$ is defined above. In a preferred embodiment, the solvent is ether. This method is both cheap and easy, due, in part, to the wide availability and low cost of many of the parent phospholipid compounds (e.g., sphingophospholipids and phosphoglycerides), easy synthesis of alkyl triflates, and the rapid reaction that occurs at or near room temperature. In a preferred embodiment of the present invention, the parent phospholipid compound is phosphatidylcholine, which may be obtained from egg yolk, other natural sources, or synthesized.

Coupled with the general availability of the parent phospholipid, this method for synthesis provides a broad spectrum of phosphonium derivatives having polar head groups and lipid side chains varying in both their steric and electronic properties, particularly hydrophobicity and hydrophilicity. Thus, the methods and compounds of the present invention essentially allow one to tune the properties of a phospholipid to nearly any desired state.

The present invention also provides for improved methods of transfection using the phospholipids of the present invention. Using standard techniques, nucleic acids can be transfected into cells, in vitro or in vivo, with high efficiency. The present invention further provides for improved methods of drug delivery.

The present invention also provides for improved methods of treating patients having diseases or ailments amenable to treatment with nucleic acids, oligonucleotides or drugs. Such diseases include those arising from infection with a pathogen, in which case treatment may comprise administration of an antisense oligonucleotide targeted to an endogenous nucleic acid within the pathogen that is essential to a developmental, metabolic, or reproductive function of the pathogen or by delivery of a drug. Other diseases include those arising from a DNA deficiency. Such deficiency may be the lack of essential DNA or a mutation (such as a deletion, alteration, or addition of one or more nucleotides) resulting in under- or over- expression of a gene or expression of an abnormal protein. In such a case, treatment may comprise lipofection of normal nucleic acid.

DETAILED DESCRIPTION OF THE INVENTION

Figure 1:
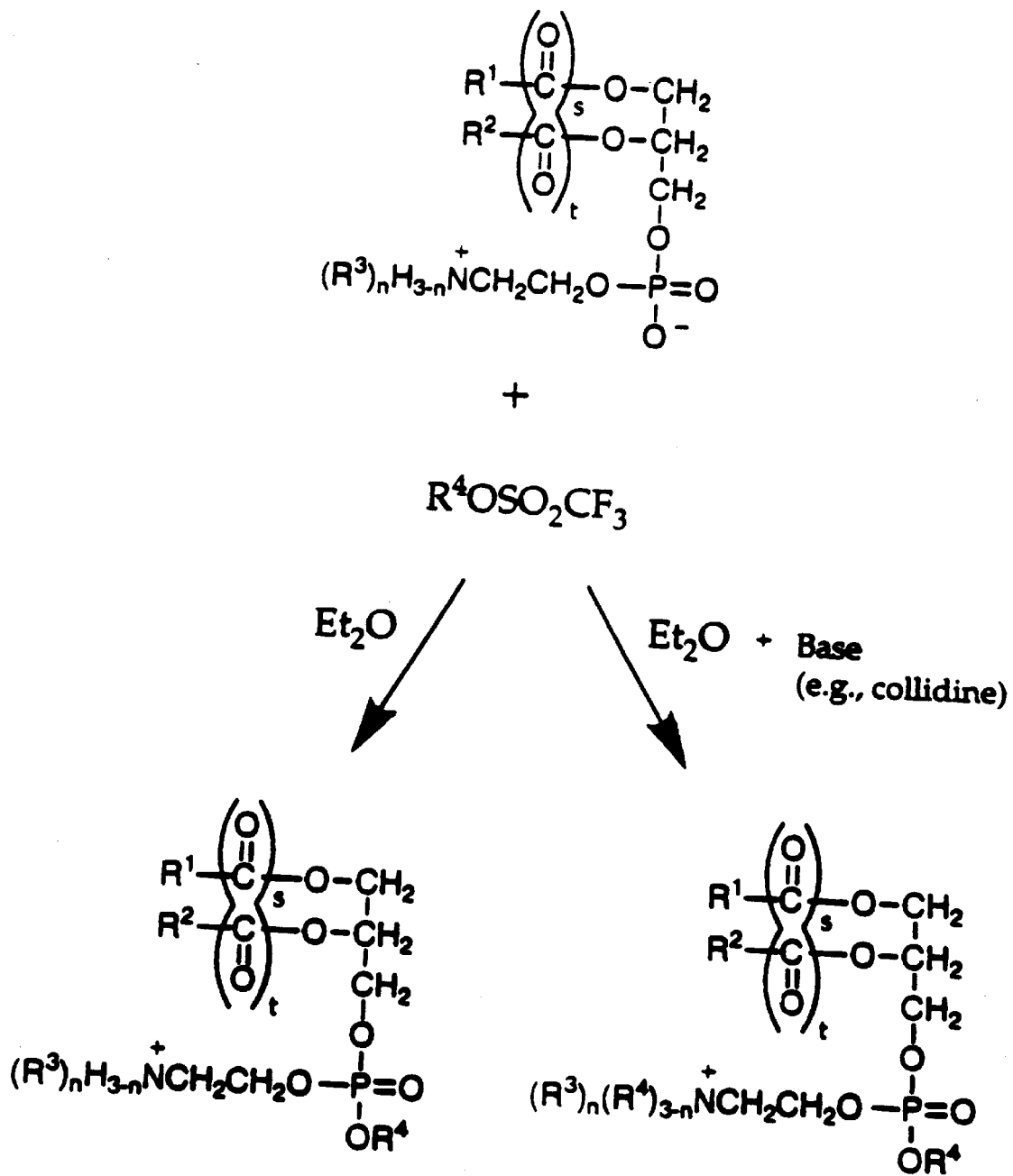
FIG. 1 depicts the synthetic method for alkylating phosphoglycerides to produce O- substituted derivatives.

The present invention provides novel cationic phospholipids, liposomes comprising these phospholipids, liposome nucleic acid aggregates, methods for transfecting nucleic acids in vitro and in vivo comprising contacting a cell or cells with the liposome-nucleic acid aggregates, and methods for treating diseases arising from infection or a DNA deficiency treatable by in vivo delivery of nucleic acids.

In the first aspect of the present invention, novel cationic phospholipids are disclosed. These cationic phospholipids are capable of forming liposomes and transfecting nucleic acids into cells. An attractive feature of this class of compounds is that they can be synthesized from cheap, readily obtainable parent phosphoglyceride compounds. These phosphoglyceride compounds have the following structure:

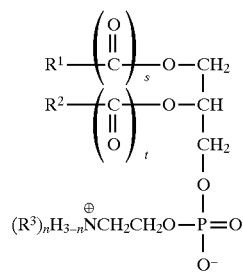

wherein
  $R^1$ and $R^2$ independently are H or $C_1$ to about $C_{24}$ straight or branched alkyl, alkenyl, or alkynyl chains optionally substituted with a dansyl, NBD, DPH, carbocylclic aromatic, or heterocyclic moiety,
  $R^3$ is hydrogen or methyl,
  n is 0, 1, 2, or 3,
  s is 0 or 1, and
  t is 0 or 1,
  provided that $R^1$ and $R^2$ are not both H and that when $R^1$ is H, s is 0, and that when $R^2$ is H, t is 0.

In a preferred embodiment of the present invention, the parent phosphoglyceride compound is naturally occurring or readily derived from a naturally occurring compound. In a particularly preferred embodiment, the parent phosphoglyceride compound is phosphatidylcholine. Phosphatidylcholine is extremely cheap and easily obtainable from egg yolk.

The novel phospholipids of the present invention obtained from the above reactant compounds have the following structure:

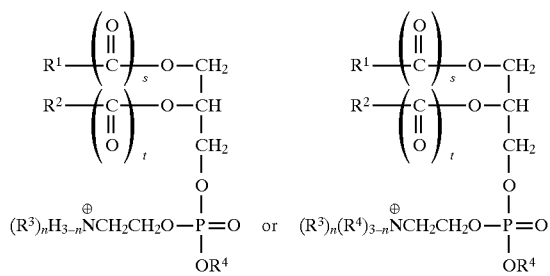

wherein all definitions described above for the parent compound hold, $R^4$ is $C_1$ to about $C_{24}$ straight or branched alkyl, alkenyl, or alkynyl chains optionally substituted with dansyl, NBD, DPH, carbocylclic aromatic, or heterocyclic moiety, or $R^4$ is a $C_1$ to about $C_6$ straight or branched chain ester, aldehyde, ketone, ether, haloalkyl, azidoalkyl, or tetraalkylammonium.

As used herein, the term "alkenyl" refers to a moiety having from 1 to 6 double bonds. "Alkynyl" refers to a moiety having 1 or 2 triple bonds. A "branched chain" has from 1 to 4 branching methyls and up to 2 cyclopropyl groups. A "carbocyclic aromatic" has up to 4 rings, which may be fused or spiro, and 5 or 6 carbon atoms per ring. "Heterocyclic moiety" means 1 to 3 rings having 5 or 6 atoms in the ring or rings and up to 2 oxygen or nitrogens per ring.

In a preferred embodiment, the compound is the phosphotriester derivative of a naturally occurring compound. In a particularly preferred embodiment, the compound is the phosphotriester derivative of phosphatidylcholine. In another preferred embodiment, the compound is the ethyl phosphotriester derivative of phosphatidylcholine. In yet another preferred embodiment, $R^1$ or $R^2$ is an NBD substituted $C_6$–$C_{12}$ alkyl. As is described more fully below, we have prepared a number of these compounds.

A second group of novel cationic phospholipids is derived from a class of sphingophospholipid related compounds having the general structure:

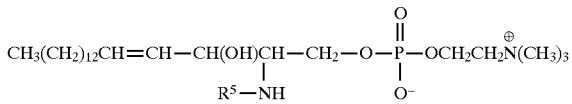

where $R^5$ is a fatty acid or related carboxylic acid having the same structure as $R^1$, supra. The sphingophospholipids are alkylated in the same manner as the phosphoglyceride compounds. The alkyl group adds to the same position on the phosphate oxygen as on the phosphoglycerides to yield:

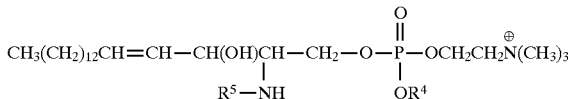

As will be described more fully below, it has been found that these cationic phospholipids of the present invention are effective agents for transfecting nucleic acids and drugs.

In a second aspect of the present invention, a novel method of synthesizing the aforementioned phospholipids is disclosed. The synthetic method of the present invention comprises mixing an $R^4$ substituted trifluoromethanesulfonate (triflate) with a parent phosphoglyceride or sphingophospholipid in a suitable solvent, wherein $R^4$ is $C_1$ to about $C_{24}$ straight or branched alkyl, alkenyl, or alkynyl chains optionally substituted with a dansyl, NBD, DPH, carbocylclic aromatic, or heterocyclic moiety, or $R^4$ is a $C_1$ to about $C_6$ straight or branched chain ester, aldehyde, ketone, ether, haloalkyl, azidoalkyl, or tetraalkylammonium. By suitable solvent it is meant any solvent capable of dissolving both reactant species and that itself does not undergo a chemical reaction with the starting materials, intermediates or products. Suitable solvents will be recognized or can be determined in a routine manner by those skilled in the art. In a preferred embodiment, the solvent is diethyl ether. The reaction proceeds rapidly at room temperature to yield nearly instantaneously the phospholipids described above. The products can then be purified by any suitable means. A preferred method of purification is by simple batch chromatography on $SiO_2$.

Under neutral conditions, the reaction proceeds by transferring the triflate substituent to a non-bridging oxygen of the phosphate to form a phosphotriester. In the presence of a sterically hindered base (e.g., collidine) and when $R^3$ is hydrogen, both the phosphate oxygen and the ethanolamine nitrogen will be substituted. See FIG. 1.

A preferred method of the present invention comprises reaction of an ethereal solution of phosphoglyceride parent compound with an alkyl-trifluoromethanesulfonate. The result is a nearly instantaneous, clean conversion to the substituted phosphotriester derivative of the phosphoglyceride parent compound as the triflate salt. Purification is then by simple batch chromatography on $SiO_2$, which affords pure alkyl-phospholipid triester in 85% isolated yield on a 1-gram scale. In a preferred embodiment, the alkyl group is an ethyl moiety.

Substituted triflates are easily made according to the following reaction

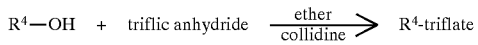

Triflic anhydride is available from Alrich®, for example.

Using the methods of the present invention, we have conducted the following syntheses:

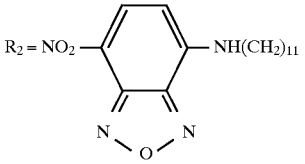

wherein t=s=1, n=3, and $R^3=CH_3$. Compounds 10 and 11 were prepared at −78° C. The functional groups in compounds 10 and 11 can be modified to allow for conjugation of the cationic lipid with other molecules.

The availability of both naturally occurring and synthetic phospholipids coupled with the wide availability of alkyl triflates provides a unified route to the synthesis of a diverse array of cationic lipids. This should provide the ability to tune the molecular and biological properties of the transfection reagent and provide a means of investigating the molecular basis of lipid-based transfection. Finally, the basis of the cationic lipid in a natural phospholipid skeleton provides for the attenuation of long-term cytotoxicity through metabolic transformation of the compound to a natural product.

While the preferred method of producing the compounds of the present invention is by the novel triflate method described, those of ordinary skill in the art will recognize that other art recognized methods of synthesis may be used. For instance, other alkylating agents that may be used include alkyl iodides, alkyl tosylates, dialkylsulfates, and trialkyl oxonium wherein the anion is $BF_4^-$.

Because of their unique steric and electronic properties, the modified cationic phospholipids synthesized by the foregoing methods generate a novel class of liposomes that are very effective in the lipofection of nucleic acids. As used herein, the term "liposome" is meant to encompass all compositions of phospholipids (and/or other amphiphiles) that aggregate in aqueous solution, including micelles, as well as cubic and hexagonal phases.

The liposomes of the present invention comprise one or more of the phospholipids of the present invention. Liposomes according to the invention optionally have one or more other amphiphiles. The exact composition of the liposomes will be depend on the particular circumstances for which they are to be used. Those of ordinary skill in the art will find it a routine matter to determine a suitable composition. The liposomes of the present invention comprise at least one phospholipid of the present invention. In a preferred embodiment, the liposomes of the present invention consist essentially of a single type of phospholipid according to the invention. In another preferred embodiment, the liposomes comprise mixtures of compounds according to the present invention. In yet another preferred embodiment, the liposomes of the present invention comprise one or more phospholipids of the present invention in mixture with one or more natural or synthetic lipids, e.g., cholesterol. In still another preferred embodiment, the liposomes consist essentially of the ethyl phosphotriester derivative of phosphatidylcholine. It is a routine matter, using techniques well known in the art, to determine an appropriate and optimal ratio of components where mixtures of phospholipids are used.

Liposomes are constructed by well known techniques. E.g., *Liposome Technology*, Vols. 1–3 (G. Gregoriadis, Ed., CRC Press, 1993) Lipids are typically dissolved in chloroform and spread in a thin film over the surface of a tube or flask by rotary evaporation. If liposomes comprised of a mixture of lipids is desired, the individual components are mixed in the original chloroform solution. After the organic solvent has been eliminated, a phase consisting of water optionally containing buffer and/or electrolyte is added and the vessel agitated to suspend the lipid. The suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires some minutes depending upon conditions, kind, and quality of the sonicator. Commonly, lipid concentrations are 1 mg/ml of aqueous phase, but could easily be a factor of ten higher or lower.

In a third aspect of the invention, a novel method of lipofection is provided comprising contacting cells to be transformed with a solution of liposome-nucleic acid aggregates. Liposome-nucleic acid aggregates may be prepared by adding an appropriate amount of nucleic acid to a liposome solution. For transfection, the weight ratio of cationic lipid to DNA is from slightly over 1:1 to perhaps 10:1. The amount of DNA can vary considerably, but is normally a few to a few tens of micrograms per standard culture dish of cells. Conditions may vary widely, and it is a routine matter and standard practice to optimize conditions for each type of cell, as suppliers of commercial materials recommend. Optimization involves varying the lipid to DNA ratio as well as the total amount of aggregate.

As has been noted, there is currently some uncertainty regarding the precise way in which nucleic acids and phospholipids (and other amphiphiles) interact. In addition, the structure formed both before and during the transfection process is not definitively known either. The present invention, however, is not limited by the particular structural type of complex formed by the liposomes of the present invention and the nucleic acids to be transfected. As used herein, therefore, the phrase "liposome-nucleic acid aggregate" means any association of liposomes and nucleic acids that is capable of lipofection.

The lipid-nucleic acid aggregate is added to the cells, in culture medium, and left for some tens of minutes to several hours to perhaps overnight. Usually serum is omitted from the culture medium during this phase of transfection. Subsequently, the medium is replaced with normal, serum-containing medium and the cells are incubated for hours to days or possibly cultured indefinitely.

Figure 2:
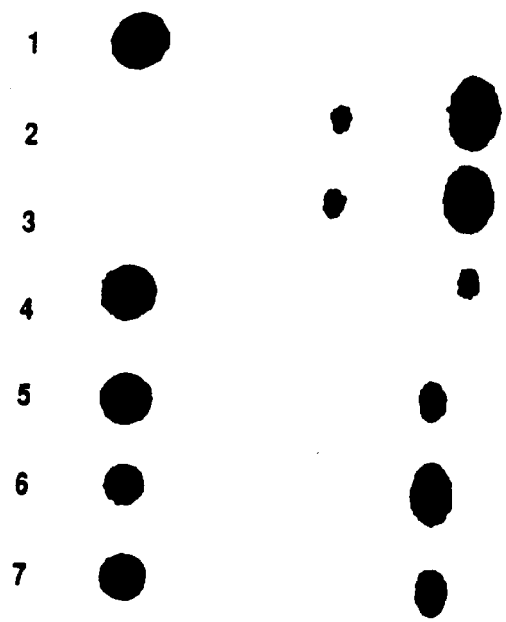
FIG. 2 is an autoradiogram showing the results of a chloramphenicol acetyl-transferase assay of extracts of L cells and Rcho-1 cells transfected with RSV-CAT DNA.

Both P(O) methylated phosphatidylcholine (MePC$^+$, 2) and ethylated phosphatidylcholine (EtPC$^+$ 3) are effective mediators of DNA transfection into eukaryotic cells, showing efficiency in RSV-CAT transfections (e.g., Gorman et al., Mol. Cell. Biol. 2, 1044 (1982); de Wet et al., Mol. Cell. Biol. 7, 725 (1987)) into L cells and Rcho-1 cells equivalent to or better than that observed with "LIPOFECTIN" (Example 3 and FIG. 2). Unlike existing transfection reagents made from cationic detergents, MePC$^+$ (2) and ETPC$^+$ (3) are effective transfection reagents in the absence of phosphatidyethanolamine (PE). The reasons for this difference are not clear at present, but recent studies have indicated that the PE co-lipid requirement for "LIPOFECTIN" varies with the cell type and culture age. Jarnagin et al., Nucl. Acids Res. 20, 4205 (1992). Interestingly, the fluorescent nitrobenzofurazan (NBD) tagged lipid 9 mediated transfection better than EtPC$^+$ (3), as cells transfected using mixtures of EtPC$^+$ (3) and 2 showed increasing CAT activity as the proportion of 9 in the mixture increased. This suggests that the nature of the fatty acid substituent in the phosphoglyceride parent compound plays an important role in determining DNA transfection efficiency. The ability to prepare a diverse array of cationic phosphatidylcholine derivatives using the methods of the present invention will allow a more systematic investigation of the structural factors involved in DNA transfection by cationic liposomes and provide for a wider variety of cationic liposomes useful for lipofection.

Myriad nucleic acids may be associated with the liposomes of the present invention and transfected. These include DNA, RNA, DNA/RNA hybrids (each of which may be single or double stranded), including oligonucleotides such as antisense oligonucleotides, chimeric DNA-RNA polymers, and ribozymes, as well as modified versions of these nucleic acids wherein the modification may be in the base, the sugar moiety, the phosphate linkage, or in any combination thereof.

From the foregoing it will be clear to those skilled in the art that the liposomes of the present invention are useful for both in vitro and in vivo application. The liposomes of the present invention will find use for nearly any in vitro application requiring transfection of nucleic acids into cells—one such example being in the process of recombinant production of a protein.

The nucleic acids may comprise an essential gene or fragment thereof of which the target cell or cells is deficient in some manner, such as lacking the gene or wherein the gene is mutated resulting in under- or over- expression. The associated nucleic acids may also comprise antisense oligonucleotides. Such antisense oligonucleotides may be constructed to inhibit expression of a target gene. The foregoing are but examples of nucleic acids that may be used with the present invention and are not intended and should not be construed to limit the invention in any way. Those skilled in the art will appreciate that other nucleic acids will be suitable for use in the present invention as well.

The liposomes of the present invention are also useful for drug delivery. As used herein, the term "liposome-drug aggregate" means any association of liposomes and drugs capable of delivering the drug to cells. The term "drug," as used herein, refers to any non-nucleic acid compound that is or can be used as a therapeutic, be it protein or non-protein in nature. The efficiency of delivery of drugs is improved greatly if the drug is hydrophobic. The uptake of cationic drugs may be increased if one includes a counterion such as a fatty acid or if the liposomes are made up in an aqueous solution of high ionic strength. The particular liposome and encapsulation process will depend upon the drug. It is a routine matter, however, to determine the appropriate conditions for drug delivery using liposomes.

Phospholipid-assisted drug delivery may be accomplished in the following manner. For drugs that are soluble in organic solvents, such as chloroform, the drug and cationic lipid are mixed in solvents in which both are soluble, and the solvent is then removed under vacuum. The lipid-drug residue is then dispersed in an appropriate aqueous solvent, which, in a preferred embodiment, is sterile physiological saline. The suspension then may optionally be subjected to up to several freeze/thaw cycles. It is then sonicated, either merely to reduce the coarseness of the dispersion or to reduce the particle size to 20–30 nm diameter, depending upon whether large or small particle size is most efficacious in the desired application. For some applications, it may be most effective to generate extruded liposomes by forcing the suspension through a filter with pores of 100 nm diameter or smaller. For some applications, inclusion of cholesterol or natural phospholipids in the mixture used to generate the lipid-drug aggregate may be appropriate. The liposome-drug aggregate may then be delivered in any suitable manner.

For drugs that are soluble in aqueous solution and insoluble in organic solvents, the lipid mixture to be used for the lipid dispersion or liposomes is coated on the inside surface of a flask or tube by evaporating the solvent from a solution of the mixture. In general, for this method to be successful, the lipid mixture must be capable of forming vesicles having single or multiple lipid bilayer walls and encapsulating an aqueous core. The aqueous phase containing the dissolved drug, preferably a physiological saline solution, is added to the lipid, agitated to generate a suspension, and then optionally frozen and thawed up to several times. If it is desired to generate small liposomes, the suspension is subjected to ultrasonic waves for a time necessary to reduce the liposomes to the desired average size. If large liposomes are desired, the suspension is merely agitated by hand or on a vortex mixer until a uniform dispersion is obtained, i.e., until visually observable large particles are absent. If the preparation is to have the drug contained only within the liposomes, then the drug in the aqueous phase is eliminated by dialysis or by passage through a gel-filtration chromatographic column (e.g., agarose) equilibrated with the aqueous phase containing all normal components except the drug. Again, the lipid mixture used may contain cholesterol or natural phospholipids in addition to the cationic compounds of the present invention. The liposomedrug aggregate may then be delivered in any suitable manner.

The fourth aspect of the invention comprises novel methods of treating diseases arising from infection by a pathogen or from an endogenous DNA deficiency. These methods comprise administering a liposome-nucleic acid aggregate and/or liposome-drug aggregate solution to a mammal suffering from a pathogenic infection or DNA deficiency. If the disease is the result of infection by a pathogen, the nucleic acid may be, for example, an antisense oligonucleotide targeted against an DNA sequence in the pathogen that is essential for development, metabolism, or reproduction of the pathogen. If the disease is a DNA deficiency (i.e., wherein certain endogenous DNA is missing or has been mutated), resulting in under- or over- expression, the nucleic acid may be the normal DNA sequence.

Several methods of in vivo lipofection have been reported. In the case of whole animals, the lipid-nucleic acid aggregate may be injected into the blood stream, directly into a tissue, into the peritoneum, instilled into the trachea, or converted to an aerosol, which the animal breathes. Zhu et al., *Science* 261, 209–211 (1993) describe a single intravenous injection of 100 micrograms of a mixture of DNA and DOTMA:dioleoylphosphatidylethanaolamine that efficiently transfected virtually all tissues. Nabel et al., supra, used a catheter to implant liposome-DNA aggregates in a blood vessel wall, resulting in successful transformation of several cell types, including endothelial and vascular smooth muscle cells.

Stribling et al., *Proc. Natl. Acad. Sci. USA* 89, 11277–11281 (1992), demonstrated that aerosol delivery of a chloramphenicol acetyltransferase (CAT) expression plasmid complexed to cationic liposomes produced high-level, lung-specific CAT gene expression in mice in vivo for at least 21 days. They described the following procedure: Six milligrams of plasmid DNA and 12 $\mu$mol of DOTMA/DOPE liposomes were each diluted to 8 ml with water and mixed; equal volumes were then placed into two Acorn I nebulizers (Marquest, Englewood, Colo.); animals were loaded into an Intox small-animal exposure chamber (Albuquerque) and an air flow rate of 4 L/min was used to generate the aerosol (about 90 min were required to aerosolize this volume) the animals were removed from the chamber for 1–2 hours and the procedure was repeated. This protocol is representative of the aerosol delivery method.

The following Examples are presented for illustrative purposes only and are not intended, and should not be construed, to limit the invention in any manner.

EXAMPLES

Example 1

Synthesis of O-Methyl and O-Ethyl Phosphatidylcholine

Phosphatidylcholine was obtained as a $CHCl_3$ solution (Avanti Polar Lipids, Inc., Alabaster, Ala.). Methyl trifluoromethanesulfonate and ethyl trifluoromethanesulfonate were obtained from Aldrich Chemical Co. (St. Louis, Mo.) and distilled prior to use. Ethyl ether was distilled from lithium aluminum hydride prior to use.

The triflate ester (1.0 mmol) was added dropwise to a solution of phosphatidylcholine (1.0 mmol) in 20 ml of ethyl ether stirred under an nitrogen atmosphere. Thin-layer chromatographic analysis ($SiO_2$, 65:25:4 $CHCl_3$:$CH_3OH$:$H_2O$; detection with phosphomolybdate spray) indicated complete conversion of phosphatidylcholine ($R_f$=0.25) to alkyl $PC^+$ ($R_f$=0.60) within 30 minutes. The reaction mixture was poured onto a pad of $SiO_2$ (4 cm diameter by 2 cm high) and the ether was pulled through by aspirator vacuum. The $SiO_2$ pad was washed 3 times with 10 ml portions of $CHCl_3$:$CH_3OH$ (10:1). Product-containing fractions were pooled and evaporated in vacuo.

The methyl phosphotriester was obtained in 85% yield. The ethyl phosphotriester was obtained in 80% isolated yield after a reaction period of 4 hours.

Analysis of the methyl phosphotriester of phosphatidylcholine by 600 MHz $^1$H-NMR revealed a pair of doublets (3H, J=12 Hz) at $\delta 3.85$, characteristic of the expected diastereomeric mixture of phosphate methyl esters.

Example 2

Liposome Metabolism and Stability

The metabolism of these cationic lipids was investigated using the fluorescent derivative 9. Mouse L-cell cultures were treated with the fluorescent derivative 9, with and without DNA, in the same way as the standard transfection procedure was carried out in Example 3, infra. After 24 hours of incubation, the cells were scraped from the plate and centrifuged to isolate them as a wet pellet. Lipid was extracted from the cells with milliliter portions of chloroform:methanol (2:1). The chloroform lower phase of the extract was removed and concentrated. Thin layer chromatography (TLC) of the concentrated extract on silica gel plates with chloroform:methanol:water (65:25:4) revealed a major spot in the position of the original fluorescent lipid and a second, less intense spot with an $R_f$ that was approximately that expected for 12-NBD-aminodecanoic acid. Based on the relative fluorescent intensity of the two spots, about one third of the original compound was hydrolyzed in approximately the time required for the typical transfection of cultured cells.

In the absence of cells, aqueous $ETPC^+$ (3) is quite stable; using thin layer chromatography, no measurable degradation is observed after several days at room temperature. Samples have beeen kept in chloroform at $-20°$ C. for more than 2 years without showing signs of degradation.

To further examine the metabolism of these lipids, 9 was treated with purified phospholipases obtained from various sources following standard procedures. W. W. Christie, *Lipid Analysis* (2nd ed., Pergamon Press, Oxford, 1982). Typically, 50–100 micrograms of 9 in 50–250 $\mu$l of ethyl ether were shaken with 50–250 $\mu$l of enzyme in buffer containing, if appropriate for the function of the enzyme, calcium chloride. Several microliter samples were taken at intervals for TLC analysis on silica gel plates with chloroform:methanol:water or chloroform:methanol:concentrated ammonia, both 65:25:4. No detectable reaction was observed with phospholipase C from *Clostridium perfringens*. Phospholipase D from cabbage, brussels sprouts, peanut, and *Streptomyces chromofuscus* showed very slow degradation of 9 compared with that of PC. All enzymes except that extracted from brussels sprouts (by us) were commercial preparations obtained from Sigma (St. Louis, Mo.).

The product of phospholipase D action on 9 has not yet been firmly identified, although it is clear that it is neither 1 nor phosphatidic acid. It is possible that the product is phosphatidylethanol based on its chromatographic properties. The choline group is thus not as readily lost from 9 as from phosphatidylcholine under the influence of the enzyme used.

Treatment with phospholipase A2 (Naja naja) produced 12-(NBD-amino)dodecanoic acid, although several-fold more slowly than observed for the PC control reaction. Cellular metabolism of $EtPC^+$ (3) may thus proceed via phospholipase A-mediated hydrolysis, with loss of the choline moiety occurring much more slowly via the action of phospholipase D, although clearly such a conclusion needs to be regarded cautiously because intracellular lipases may exhibit different activities than those used in our in vitro assays.

Example 3

Lipofection of Cultured L and Rcho-1 Cells

Mouse L cells were grown in Dulbecco's modified Eagle's medium with 10% calf serum, 100 U/ml penicillin, 100 μg/ml streptomycin, and glutamine. Rcho-1 cells were grown in RPMI 1640 medium containing 10% heat inactivated fetal calf serum, 50 μM 2-mercaptoethanol, 1 mM sodium pyruvate, 100 U/ml penicillin, and 100 μg/ml streptomycin. Both cell lines were grown at 37° C. in a 5% $CO_2$ atmosphere.

A $CH_3Cl_3$ solution of lipid was dried in vacuo and suspended in sterile $H_2O$ at 10 mg/ml (NBD-tagged lipid was suspended at 1 mg/ml due to limited solubility) by vortexing. This suspension was sonicated for 30 seconds using the microprobe of a Branson 400W sonicator at lowest power. This suspension was diluted to 1 mg/ml and further treated by extrusion through a 1000 Å ultrafilter to produce more homogeneous liposomes.

An aqueous suspension of liposomes (80 μg of lipid) was mixed with 10 μg of RSV-CAT DNA and kept at ambient temperature for 20 minutes. Cells were washed with phosphate buffered saline, and the medium was replaced with either DME or RPMI. Once a cloudy white precipitate had formed in the liposome-DNA mixture, the solution was added dropwise to the cells. The plates were then gently swirled and incubated 10–24 hrs at 37° C. under 5% $CO_2$. The medium was replaced by complete medium, and the cells were harvested 48 hrs after addition of DNA. Transfections involving "LIPOFECTIN" (using 30 μg) were performed according to the published procedures of Gibco-BRL. Cell extracts were prepared and assayed for chloramphenicol acetyltransferase and luciferase activities. The autoradiogram is presented in FIG. 2. The following table identifies the transfecting reagents for each lane appearing in the FIG. 2 autoradiogram:

| Cell Type | Lane | Reagents |
| --- | --- | --- |
| Mouse L | 1 | 1000 Å vesicle EtPC+ (3) |
|  | 2 | 1000 Å vesicle EtPC+ (3) + RSV-CAT DNA |
|  | 3 | sonicated EtPC+ (3) + RSV-CAT DNA |
|  | 4 | "LIPOFECTIN" + RSV-CAT DNA |
| Rcho-1 | 5 | 1000 Å vesicle EtPC+ (3) + RSV-CAT DNA |
|  | 6 | sonicated EtPC+ (3) + RSV-CAT DNA |
|  | 7 | "LIPOFECTIN" + RSV-CAT DNA |

As can be seen from the autoradiogram, EtPC+ (3) is as effective a transfecting agent as "LIPOFECTIN".

Following the same protocol, we studied the relative transfection efficiency of the NBD tagged lipid (9) and that of EtPC+ (3). 10 μg of RSV-CAT and 80 μg of lipid were used. The results are displayed in FIG. 3. The following table identifies the contents of the lanes:

| Lane | Lipid |
| --- | --- |
| 1 | no lipid |
| 2 | NBD-PC |
| 3 | EtPC+ |
| 4 | 1:1 EtPC+/NBD-EtPC+ |
| 5 | NBD-EtPC+ |

Figure 3:
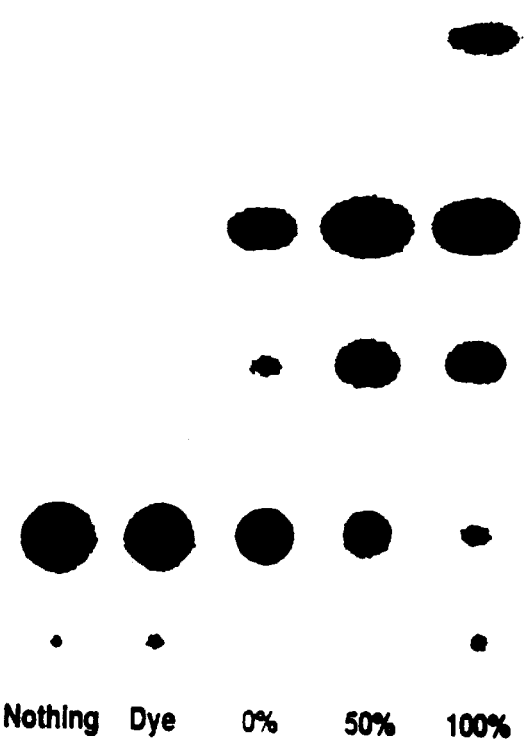
FIG. 3 presents the results of a CAT assay of the relative transfection efficiency of NBD-EtPC+.

The results presented in FIG. 3 show that NBD-tagged lipid (11) mediated transfection somewhat better than EtPC+ (3). This suggests that the nature of the fatty acid substituents play an important role in determining DNA transfection efficiency.

Example 4

Lipofection of Cultured Baby Hamster Kidney and Niemann-Pick (Type A) Fibroblast Cells EtPC+ (3) was used to transfect the protein RAB-7 gene. A vector containing the gene for RAB-7 and the T7 polymerase promoter was constructed. It was transfected into baby hamster kidney and Niemann-Pick (type A) cells. The cells were simultaneously infected with a recombinant vaccinia virus containing the T7 polymerase. The ratio of EtPC+ (3) to DNA was 5:1 by weight. Expression of the RAB-7 gene was determined by measuring cells stained with antibodies to the RAB-7 protein. Under the conditions used (which were not optimized for EtPC+), transfection efficiency (as measured by the percent of cells expressing the RAB-7 gene) was 30–40% for BHK cells and about 20% for the fibroblasts. These results were very similar to those obtained with the commercial product "LIPOFECTIN".

Example 5

Lipofection of Cultured Human Erythroleukernia (K562) Cells

The lipofection of cultured human erythroleukemia (K562) cells using EtPC+ (3) was compared to "LIPOFECTIN". Either 10 or 50 μg of EtPC+ (3) or 30 μg of "LIPOFECTIN" were mixed with either 5 μg of pRSV-CAT or 5 μg each of pGAL4-HSF1 and pGAL4-CAT. The lipid-DNA aggregate was then added to the cells. After 48 hours, the cells were assayed for CAT activity using the conventional chromatographic radioassay. By visual examination of the autoradiogram, the results for EtPC+ (3) and for "LIPOFECTIN" transductions were very similar.

Example 6

Lipofection of Whole Animals

To lipofect whole animals, the general procedure of Zhu et al., supra, may be used. Per 20 g animal weight, 100 μg of DNA as the appropriate vector, complexed with approximately 600 μg of cationic lipid, is injected intravenously. It is expected that, for optimal results, the amount of DNA and the ratio of cationic lipid to DNA will need to be varied and expression of the desired trait evaluated for each amount and ratio. Lipid is dispersed in the same way as for in vitro transfection.

For localizing the dose and preferentially treating specific tissues or organs, various procedures may be applied, such as injections directly into the organ or tissue, delivery by canula or injection to ducts, vessels or passages leading to the organ or tissue of interest, or direct surface application, either manually or through an aerosol vapor, for example, to the lungs.

We claim:

1. A liposome-drug aggregate comprising one or more nucleic acids and one or more liposomes, each liposome comprising one or more cationic phospholipids having the structure:

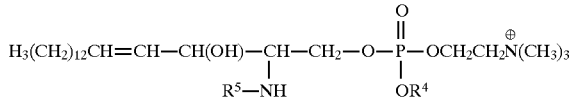

wherein $R^4$ is $C_1$ to about $C_{24}$ straight or branched alkyl, alkenyl, or alkynyl chain optionally substituted with a carbocyclic, aromatic, or heterocyclic moiety, or $R^4$ is a $C_1$ to about $C_6$ straight or branched chain ester, aldehyde, ketone, ether, haloalkyl, azidoalkyl, or tetraalkylammonium, $R^5$ is H or a $C_1$ to about $C_{24}$ straight or branched alkyl, alkenyl, or alkynl chain optionally substituted with carbocyclic, aromatic, or heterocyclic moiety, or $R^4$ is a $C_1$ to about $C_6$ straight or branched chain ester, aldehyde, ketone, ether, haloalkyl, azidoalkyl, or tetraalkylammonium.

2. The liposome-drug aggregate of claim 1 wherein the heterocyclic moiety is selected from the group consisting of dansyl, nitrobenzofurayan, and 1,6 diphenyl-1,3,5 hexatriene.

3. A method of treating a pathogen-associated disease comprising administering a therapeutically effective amount of a liposome-drug aggregate according to claim 1, wherein the drug inhibits an essential metabolic or reproductive function of a pathogen.

* * * * *

UNITED STATES PATENT AND TRADEMARK OFFICE
CERTIFICATE OF CORRECTION

PATENT NO. : 5,855,910
DATED : January 5, 1999
INVENTOR(S) : Gary W. Ashley, et al.

It is certified that error appears in the above-identified patent and that said Letters Patent is hereby corrected as shown below:

Figure 1 lists the middle -C group on the right hand side in each of the three chemical structures as "-CH$_2$" and should read -- -CH --

Signed and Sealed this

Twelfth Day of December, 2000

Attest:

Q. TODD DICKINSON

*Attesting Officer*      *Director of Patents and Trademarks*